(12) United States Patent
Dunlop et al.

(10) Patent No.: US 12,042,552 B2
(45) Date of Patent: Jul. 23, 2024

(54) LATE-STAGE PRODUCT DIFFERENTIATION PROCESS FOR PERSONAL CARE PRODUCTS

(71) Applicant: The Procter & Gamble Company, Cincinnati, OH (US)

(72) Inventors: David Scott Dunlop, Mason, OH (US); Anthony William Hill, Cincinnati, OH (US); Anne Sloan, Cincinnati, OH (US); Michael Kai-Chiau Chang, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 352 days.

(21) Appl. No.: 17/400,376

(22) Filed: Aug. 12, 2021

(65) Prior Publication Data
US 2022/0071879 A1     Mar. 10, 2022

Related U.S. Application Data

(60) Provisional application No. 63/076,541, filed on Sep. 10, 2020.

(51) Int. Cl.
| | | |
|---|---|---|
| A61Q 5/02 | (2006.01) | |
| A61K 8/19 | (2006.01) | |
| A61K 8/365 | (2006.01) | |
| A61K 8/44 | (2006.01) | |
| A61K 8/46 | (2006.01) | |
| A61K 8/49 | (2006.01) | |
| A61K 8/73 | (2006.01) | |
| A61Q 13/00 | (2006.01) | |

(52) U.S. Cl.
CPC ............... *A61K 8/463* (2013.01); *A61K 8/19* (2013.01); *A61K 8/365* (2013.01); *A61K 8/44* (2013.01); *A61K 8/4926* (2013.01); *A61K 8/737* (2013.01); *A61Q 5/02* (2013.01); *A61Q 13/00* (2013.01); *A61K 2800/48* (2013.01)

(58) Field of Classification Search
CPC .......... A61K 8/463; A61K 8/19; A61K 8/365; A61K 8/44; A61K 8/4926; A61K 8/737; A61K 2800/48; A61Q 5/02; A61Q 13/00
See application file for complete search history.

(56) References Cited

U.S. PATENT DOCUMENTS

| | | | |
|---|---|---|---|
| 10,241,479 B2 | 3/2019 | Mazarei et al. | |
| 2002/0131985 A1 | 9/2002 | Shana et al. | |
| 2004/0116539 A1* | 6/2004 | Biercevicz | B01F 33/80 |
| | | | 516/21 |
| 2011/0305648 A1* | 12/2011 | Knapek | A61K 8/463 |
| | | | 424/59 |
| 2016/0128927 A1 | 5/2016 | Wei et al. | |
| 2018/0002711 A1* | 1/2018 | Schurr | C12P 7/26 |

FOREIGN PATENT DOCUMENTS

| | | |
|---|---|---|
| DE | 102010055770 A1 | 6/2012 |
| EP | 2746379 A1 | 6/2014 |
| EP | 3625321 B1 | 6/2021 |
| WO | 2016139133 A1 | 9/2016 |

OTHER PUBLICATIONS

Perfume vs. fragrance; https://en.wikipedia.org/wiki/Perfume#:~:text=Perfume%20(UK%3A%20%2F%CB%88p,living%2Dspaces%20an%20agreeable%20scent. (Year: 2019).*
15868M-WO-DW PCT Search Report and Written Opinion for PCT/US2021/071166 dated Dec. 3, 2021, 16 pages.

* cited by examiner

*Primary Examiner* — Robert A Wax
*Assistant Examiner* — John W Lippert, III
(74) *Attorney, Agent, or Firm* — David M. Weirich

(57) ABSTRACT

Process for late-stage differentiation manufacturing of a personal care composition including: formulating a base composition having a first viscosity; comparing the first viscosity of the base composition to a predetermined desired base viscosity range; adjusting the viscosity of the base composition to a second viscosity that is within the desired base viscosity range by addition of one or more viscosity modifiers; and adding one or more differentiation compositions to the base composition to create the personal care composition, wherein the personal care composition has a final viscosity within a desired final viscosity range without the need to add additional viscosity modifiers.

20 Claims, 3 Drawing Sheets

LATE-STAGE PRODUCT DIFFERENTIATION PROCESS FOR PERSONAL CARE PRODUCTS

FIELD OF THE INVENTION

The invention relates to a process for the manufacture of liquid personal care products, such as, for example, shampoos, conditioners, lotions, creams, etc., wherein a common base is used across more than one variant of the products and differentiating ingredients are added to the common base late in the manufacturing process but prior to packaging the final product.

BACKGROUND OF THE INVENTION

Liquid personal care products such as, for example, shampoos, conditioners, liquid soaps, lotions and the like are typically manufactured by mixing a number of different ingredients often pre-combined into "phases" to get to a final product. Known manufacturing processes for such products include batch processes where the different phases are mixed with each other one batch at a time in individual tanks, continuous processes where the phases are mixed as it continuously makes its way through a series of tanks, tubes or other vessels, and semi-continuous processes where some but not all of the mixing steps are continuous. Regardless of the method used, the final product is generally tested to ensure it is within the desire specifications before being directed to the filling and packing equipment. One characteristic of liquid personal care products that is often difficult to control, but is very important to consumers is viscosity. Not only is it important to have the viscosity right for any particular batch or "run" of product, it is also highly desirable for the product to have a uniform viscosity from one package to the next to give the consumer a consistent experience every time the product is used.

Current methods for ensuring the end product is within a desired viscosity range can be difficult, time consuming, and costly. Specifically, in batch processes, the viscosity of each batch of product must be measured after all phases have been combined and adjusted, as needed, to achieve the desired specifications. In many cases, this requires repeated measurement of the viscosity and addition of viscosity modifiers taking time and adding cost. In continuous and semi-continuous processes, the viscosity of the product must be repeatedly measured after all components are added and adequately mixed (very late in the manufacturing process), and typically prior to being directed to the filling and packing equipment. However, making any changes to the product at this late stage can slow down the process and/or result in down time for the filling and packing equipment, either of which can negatively impact the cost of the product. In some cases, the product may be redirected to a holding tank or other vessel where the viscosity can be adequately adjusted before being returned to the continuous process. In other processes, the out of specification product may be circulated to an earlier state in the process or may even be scrapped.

Accordingly, it would be desirable to provide a process for manufacturing personal care products that can reduce or eliminate the disadvantages of currently known batch and/or continuous processes. More particularly, it would be desirable to provide a process that allows for more efficient manufacture of liquid personal care products. Even more particularly, it would be desirable to provide a process for making liquid personal care products such that the final product is reliably within the desired specifications at the end of the manufacturing process just prior to the package filing step. Still more particularly, it would be desirable to provide a late stage differentiation proves for manufacturing liquid personal care products wherein the product resulting from the product differentiation step has certain predetermined characteristics such as, for example, pH and/or viscosity, in a predetermined range so as to reduce the need for trimming prior to filling and packing the product.

SUMMARY OF THE INVENTION

In order to address one or more of the disadvantages of current personal care composition manufacturing processes, the present invention provides a process for manufacture of personal care compositions, including late-stage differentiation of the personal care composition from a base composition, the process comprising: a) formulating the base composition in a first vessel, the base composition being an aqueous mixture of at least one surfactant and water and having a first viscosity; b) measuring the first viscosity of the base composition; c) comparing the first viscosity of the base composition to a predetermined desired base viscosity range; d) if the viscosity of the base composition is outside the predetermined desired base viscosity range, adjusting the viscosity of the base composition to a second viscosity that is within the desired base viscosity range by addition of one or more viscosity modifiers; e) moving the base composition with the second viscosity to a second vessel; and f) adding one or more differentiation compositions to the base composition creating the personal care composition, wherein the personal care composition has a final viscosity that is different from the second viscosity.

BRIEF DESCRIPTION OF THE DRAWINGS

The drawings included herein are intended to provide additional information related to certain aspects of the disclosure and are not intended to be limiting to any particular embodiment or combination of embodiments.

DETAILED DESCRIPTION OF THE INVENTION

Figure 1:
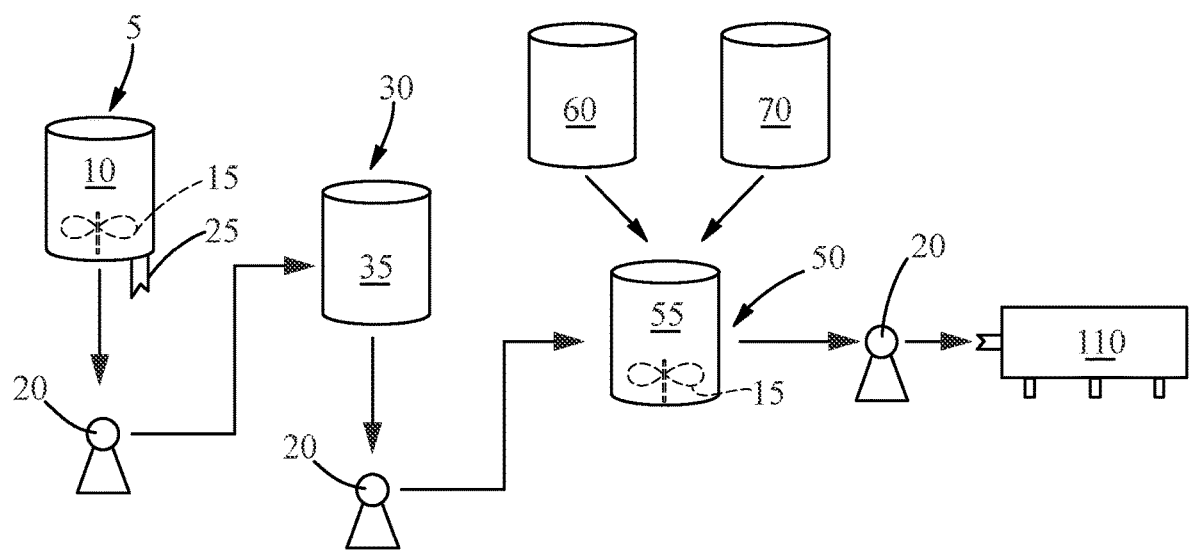
FIG. 1 is a schematic flow diagram of a first example of the new process.

The following terms have the meaning set forth in this definition section unless expressly indicated otherwise in the following description.

"Fragrance" is used herein to mean as a mixture of odoriferous components, optionally mixed with a suitable solvent diluent or carrier, which is employed to impart a desired odor. Fragrance components and mixtures thereof may be obtained from natural products such as essential oils, absolutes, resinoids, resins and concretes, as well as synthetic products such as hydrocarbons, alcohols, aldehydes, ketones, ethers, carboxylic acids, esters, acetals, ketals, nitrites and the like, including saturated and unsaturated compounds, aliphatic, carbocyclic and heterocyclic compounds.

"Personal care products" means (a) products for care of human hair, including, bleaching, coloring, dyeing, conditioning, growing, removing, retarding growth, shampooing, styling; (b) deodorants and antiperspirants; (c) products for personal cleansing, including the washing, cleaning, cleansing, or exfoliating of the skin, including the face, hands, and body, (d) color cosmetics; (e) products for application to the skin for purposes other than or in addition to cleaning, including, creams, lotions, and other topically applied products for consumer use; and fragrances, aftershaves, UV protecting compositions, facial washes or scrubs, shaving preparations, soaps, balms, oils, gels, pastes, or foaming compositions.

"Vessel" as used herein is intended to mean any type of structure that is used during the manufacturing process to contain a personal care product or any component thereof. Vessels may include, but are not limited to tanks, tubes, bowls, casks, barrels, reservoirs, chambers, pipes, hoses, etc. Vessels can be open or closed an may be separate and individual from other vessels or equipment and/or may be joined together with other vessels or equipment. Often, one or more vessels are used for mixing, reacting, movement and/or storage of materials, such as those that make up personal care products or components thereof.

As noted above, there is a need for improvements in the processes for manufacturing personal care products, specifically liquid personal care products that are formed by mixing ingredients. In particular, there is a need to improve the processes used to make variations of products that have similar base formulations or phases. The processes used to make such personal care products can be batch, continuous, and/or semi-continuous processes and can use any conventional or newly discovered equipment and controls. Historically, it has been difficult to economically produce batches, lots, or runs of liquid personal care products that are consistent in terms of certain desired characteristics, such as, for example, viscosity, pH, or the like without having to significantly modify the product prior to packaging. This late stage modification step can require additional and costly materials, require additional control equipment and product testing, and can extend the time necessary between what should be the final mixing step of the composition and the filling/packaging step. Any and all of these are disadvantages of current personal care product manufacturing processes that lead to extra costs which are either passed on to the consumer or which reduce profit for the manufacturer.

It has been discovered that one or more of the above-identified disadvantages of the current batch, semi-continuous and/or continuous processes for making personal care products can be avoided by implementing the novel and unobvious process described herein. It should be noted that different processes may be impacted differently by the improvements descried herein and, as such, not every process will require every step, while others may benefit from additional steps in addition to those specifically set forth below. It should also be noted that the detailed description in this specification should not be considered to limit the scope of the invention, but rather, along with the examples and figures, to provide information to help one of ordinary skill in the art understand the invention and how it can be used.

The process described herein is what is often referred to a "late-stage product differentiation" process, "late product differentiation" process, or "LPD" process. However, the improvements set forth herein are not limited to application in LPD processes, but can be used in any personal care product manufacturing process. LPD processes are beneficial for several reasons, including the ability to manufacture a family of products that have a similar base composition. The base composition can be any mixture of ingredients that is common to a single product made in several batches or runs or to more than one product. Typically, the base will comprise the bulk of the volume and weight of the final personal care product and generally includes the functional ingredients plus any fillers, surfactants and water. Generally, the base will constitute greater than about 50% of the weight of the final personal care product. More typically, the base will constitute greater than about 60%, about 70%, about 75%, about 80%, about 90%, about 95% about 97%, about 98%, about 99% or about 99.5% of the weight of the final personal care product.

The base composition will often contain water as a major component. The amount of water may range from about 30% to about 99.9%, from about 50% to about 95%, from about 65% to about 90%, or from about 70% to about 85% by weight of the water phase.

Generally, the base composition will contain one or more surfactants. Suitable surfactants include, but are not limited to nonionic, anionic, cationic, amphoteric, zwitterionic and surfactant combinations thereof. Further, the surfactants may be sulfated, non-sulfated (otherwise known as "sulfate-free"), sulfonated or non-sulfonated. Overall amount of surfactant may range from about 0.1 to about 50%, from about 2% to about 40%, or from about 15% to about 25% by weight of the total personal care composition.

Illustrative but not limiting examples of suitable nonionic surfactants include C10-C20 fatty alcohol or acid hydrophobes condensed with from 2 to 100 moles of ethylene oxide or propylene oxide per mole of hydrophobe; C2-C10 alkyl phenols condensed with from 2 to 20 moles of alkylene oxides; mono- and di-fatty acid esters of ethylene glycol such as ethylene glycol distearate; fatty acid monoglycerides; sorbitan mono- and di-C8-C20 fatty acids; and polyoxyethylene sorbitan available as Polysorbate 80 and Tween 80® as well as combinations of any of the above surfactants.

Other useful nonionic surfactants include alkyl polyglycosides (APGs), saccharide fatty amides (e.g. methyl gluconamides) as well as long chain tertiary amine oxides. Examples of the latter category are: dimethyldodecylamine oxide, oleyldi(2-hydroxyethyl)amine oxide, dimethyloctylamine oxide, dimethyidecylamine oxide, dimethyltetradecylamine oxide, di(2-hydroxyethyl) tetradecylamine oxide, 3-didodecyloxy-2-hydroxypropyldi(3-hydroxypropyl) amine oxide, and dimethylhexadecylamine oxide.

Illustrative but not limiting examples of anionic surfactants include Alkyl benzene sulfonates in which the alkyl group contains from 9 to 15 carbon atoms, or 11 to 14 carbon atoms in straight chain or branched chain configuration. One preferred anionic surfactant is a linear alkyl benzene sulfonate containing about 12 carbon atoms in the alkyl chain. Other suitable anionic surfactants include alkyl sulfates obtained by sulfating an alcohol having 8 to 22 carbon atoms, or 12 to 16 carbon atoms. The alkyl sulfates may have the formula ROSO3-M+ where R is the C8-22 alkyl group and M is a mono- and/or divalent cation. Yet other nonionic surfactants include paraffin sulfonates having 8 to 22 carbon atoms, or 12 to 16 carbon atoms, in the alkyl moiety. Other suitable nonionic surfactants include olefin sulfonates having 8 to 22 carbon atoms, or 12 to 16 carbon atoms. One example is sodium C14-C16 olefin sulfonate, available as Bioterge AS 40®, and alkyl ether sulfates derived from an alcohol having 8 to 22 carbon atoms, or 12 to 16 carbon atoms, ethoxylated with less than 30, or less than 12, motes of ethylene oxide. Sodium lauryl ether sulfate formed from 2 motes average ethoxylation, commercially available as Standopol ES-2® is one preferred anionic surfactant. Yet others include alkyl glyceryl ether sulfonates having 8 to 22 carbon atoms, or 12 to 16 carbon atoms, in the alkyl moiety; fatty acid ester sulfonates of the formula: RICH(SO3-M+)CO2R2 where R1 is straight or branched alkyl from about C8 to C18, or C12 to C16, and R2 is straight or branched alkyl from about C1 to C6, or primarily C1, and M+ represents a mono- or divalent cation; secondary alcohol sulfates having 6 to 18, or 8 to 16 carbon atoms; fatty acyl isethionates having from 10 to 22 carbon atoms, an example of which is sodium cocoyl isethionate; mono- and dialkyl sulfosuccinates wherein the alkyl groups range from 3 to 20 carbon atoms and each; alkanoyl sarcosinates corresponding to the formula RCON(CH3)CH2CH2CO2M wherein R is alkyl or alkenyl of about 10 to about 20 carbon atoms and M is a water-soluble cation such as ammonium, sodium, potassium and trialkanolammonium. Sodium lauroyl sarcosinate is an example thereof.

Illustrative of cationic surfactants are C8-C22 alkyl C1-C4 di-alkyl ammonium salts such as cetyl dimethyl ammonium chloride, stearyl dimethyl ammonium methosulfate, oleyl diethylammonium phosphate, and lauryl dimethyl ammonium borate. Cetrimonium chloride is a generic term for cetyl dimethyl ammonium chloride.

Exemplary amphoteric surfactants useful for the present invention include betaines which may have the general formula RN+(R1)2R2-COO— wherein R is a hydrophobic moiety selected from the group consisting of alkyl groups containing from 10 to 22 carbon atoms, or from 12 to 18 carbon atoms; alkyl aryl and aryl alkyl groups containing 10 to 22 carbon atoms with a benzene ring being treated as equivalent to about 2 carbon atoms, and similar structures interrupted by amido or ether linkages; each R1 is an alkyl group containing from 1 to 3 carbon atoms; and R2 is an alkylene group containing from 1 to about 6 carbon atoms. Sulfobetaines such as cocoamidopropyl hydroxysultaine are also suitable.

Examples of non-sulfated, or sulfate-free surfactants include, but are not limited to: taurates, isethionates, glycinates, glycosides, glutamates, betaines, sulfonates, sulfosuccinates, sulfoacetates, sarcosinates, alaninates, carboxylates, and rhamnolipds. Further, such non-sulfated surfactants can include salts including sodium, ammonium, and/or potassium.

Examples of betaines are dodecyl dimethyl betaine, cetyl dimethyl betaine, dodecyl amidopropyldimethyl betaine, tetradecyldimethyl betaine, tetradecylamidopropyldimethyl betaine, and dodecyldimethylammonium hexanoate. Most preferred is cocoamidopropyl betaine available as Tegobetaine F® sold by Th. Goldschmidt AG of Germany.

Polyols may also make up a portion of the base composition. Typical polyhydric alcohols include glycerol (also known as glycerin), polyalkylene glycols and alkylene polyols and their derivatives, including propylene glycol, dipropylene glycol, polypropylene glycol, polyethylene glycol and derivatives thereof, sorbitol, hydroxypropyl sorbitol, hexylene glycol, butylene glycol, 1,2,5-hexanetriol, ethoxylated glycerol, propoxylated glycerol and mixtures thereof. Glycerin is an example. Amounts of the polyols may range from about 0.5% to about 50%, or between about 1% and about 15% by weight of the total personal care composition.

The base composition may also include thickeners/viscosifiers in amounts from about 0.01% to about 10% by weight of the total personal care composition. The amount of thickeners can vary depending upon the consistency and thickness of the composition which is desired. Exemplary thickeners are xanthan gum, sodium carboxymethyl cellulose, hydroxyalkyl and alkyl celluloses (particularly hydroxypropyl cellulose), and cross-linked acrylic acid polymers such as those sold by B.F. Goodrich under the Carbopol trademark. Thickeners such as modified starches and clays may also be used to thicken the water phase. For instance, aluminum starch octenyl succinate (available as DryFlo® from the National Starch and Chemical Company) is particularly useful. Among the clays are included magnesium aluminum silicate (available as Veegum®), hectorite clays, montmorillonite clays, bentonites (e.g. Bentone® 38) and combinations thereof.

Water soluble conditioning agents may also be incorporated into the base composition. Cationic agents in monomeric and potymeric form are particularly useful for this purpose. Cationic cellulose derivatives, cationic starches, copolymers of a diallyl quaternary ammonium salt and an acrylamide, quaternized vinylpyrrolidone vinylimidazole polymers, polyglycol amine condensates, quaternized collagen polypeptide, polyethylene imine, cationized silicone polymer (e.g. Amodimethicone), cationic silicone polymers provided in a mixture with other components under the trademark Dow Corning 929 (cationized emulsion), copolymers of adipic acid and dimethylami nohydroxypropyl diethylenetriamine, cationic chitin derivatives, cationized guar gum (e.g. Jaguar® C—B—S, Jaguar® C-17, and Jaguar® C-16, quaternary ammonium salt polymers (e.g. Mirapol® A-15, Mirapol® AD-1, Mirapol®, ZA-1, etc., manufactured by the Miranol Division of the Rhone Poulenc Company). Examples of the monomeric cationic conditioning agents are salts of the general structure: wherein R1 is selected from an alkyl group having from 12 to 22 carbon atoms, or aromatic, aryl or alkaryl groups having from 12 to 22 carbon atoms; R2, R3, and R4 are independently selected from hydrogen, an alkyl group having from 1 to 22 carbon atoms, or aromatic, aryl or alkaryl groups having from 12 to 22 carbon atoms; and X− is an anion selected from chloride, bromide, iodide, acetate, nitrate, sulfate, methyl sulfate, ethyl sulfate, tosylate, lactylate, citrate, glycolate, and mixtures thereof. Additionally, the alkyl groups can also contain either linkages or amino group substituents (e.g., the alkyl groups can contain polyethylene glycol and polypropylene glycol moieties). The amount of each cationic conditioning agent may range from about 0.05% to about 5%, from about 0.1% to about 3%, from about 0.3% to about 2.5% by weight of the total personal care composition.

Another component that may be present in the base composition is a preservative. Suitable preservatives include EDTA salts and alkyl ester of parahydroxybenzoic acid, hydantoin derivatives, propionate salts, and a variety of quaternary ammonium compounds. Some preferred preservatives are iodopropynyl butyl carbamate, phenoxyethanol, methyl paraben, propyl paraben, imidazolidinyl urea, sodium dehydroacetate and benzyl alcohol. Often, preservatives are employed in amounts ranging from 0.01% to 2% by weight of the total personal care composition, but other amounts are contemplated depending on the particular ingredients and preservatives used as well as the environment in which the personal care product will be stored and used.

The base may include an oil phase. If so, it may the oil phase may include hydrophobic components. Generally, an oil phase will incorporate an emollient which may be selected from hydrocarbons, silicones and synthetic or vegetable esters. The amount of the emollients may range anywhere from about 0.1% to about 30%, or between about 0.5% and about 10% by weight of the total personal care product.

Hydrocarbons suitable for the present invention include, but are not limited to, isoparaffins, mineral oil, petrolatum and hydrocarbon waxes such as polyethylenes. Exemplary silicones may include cyclic or linear polydimethylsiloxanes containing from about 3 to about 9, or from about 4 to about 5, silicone atoms. Other silicones useful as an emollient material include polyalkyl siloxanes, polyalkylaryl siloxanes and polyether siloxane copolymers. Non-volatile polyalkyl siloxanes useful herein include, for example, polydimethyl siloxanes with viscosities of from about 5 to about 100,000 centistokes at 25° C. These materials may be added directly to the composition, or pre-emulsified for improved control of particle size in the final composition. The selection of emulsifier, oil-to-aqueous weight ratio, and emulsification energy may be selected to achieve the desired particle size, such as, for example, 1 micron or 40 microns, or within a range, such as about 1 micron to about 40 microns, based on the silicone hydrophobicity and viscosity. A wide range of anionic (either sulfated or "sulfate-free") and nonionic emulsifiers are suitable for emulsifying viscous silicone-based oils. Of particular utility as sulfate-free emulsifiers are ethoxylated fatty alcohols and betaines. Oil-to-aqueous weight ratios of 1:1 to 5:1 are often suitable to deliver the emulsions in a concentrated form via emulsifying in a stirred tank, via a rotor-stator mill, or with a high-energy device such as a Sonolator®, although other ratios are possible based on the desired end result and/or the particular equipment and process used.

Suitable ester emollients include, but are not limited to: alkenyl or alkyl esters of fatty acids having 10 to 20 carbon atoms. Examples include isopropyl; palmitate, isononyl isononoate, oleyl myristate, oleyl stearate, cetearyl stearate and oleyl oleate; ether-esters such as fatty acid esters of ethoxylated fatty alcohols; polyhydric alcohol esters; ethylene glycol mono- and di-fatty acid esters, diethylene glycol mono- and di-fatty acid esters, polyethylene glycol (200-6000) mono- and di-fatty acid esters, propylene glycol mono- and di-fatty acid esters, polypropylene glycol 2000 monooleate, polypropylene glycol 2000 monostearate, ethoxylated propylenbe glycol monostearate, glyceryl mono- and di-fatty acid esters, polyglycerol fatty esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters; wax esters such as beeswax, spermaceti, myristyl myristate, stearyl stearate; steroid esters, of which soya sterol and cholesterol fatty acid esters are examples thereof; vegetable ester emollients including sunflower seed oil, soy sterol esters, borage seed oil, maleated soybean oil, sucrose polycottonseedate, tribehenin, sucrose polybehenate; and mixtures thereof.

The oil phase, if any, may include one or more fatty acids. These fatty acids may have from 10 to 30 carbon atoms. Examples include pelargonic, lauric, myristic, palmitic, stearic, isostearic, hydroxystearic, oleic, linoleic, ricinoleic, arachidic, behenic and erucic acids. Generally, the amount will range from 0.1% to 25% by weight of the total personal care product.

The personal care product can be a water and oil emulsion and can be either an oil-in-water emulsion or a water-in-oil emulsion. Relative weight ratios of water to oil representing first and second phases of the base composition may range from about 1,000:1 to about 1:10, from about 100:1 to about 1:5, or from about 10:1 to about 1:2 by weight of the total personal care product.

After the base composition is formed, various differentiation ingredients may be added to form the final personal care product formulation. Typically, such differentiation ingredients will include one or more colorants, fragrances, and/or other ingredients added to the base to provide the desired end product or to differentiate a number of products having a similar base from each other. Generally, these differentiation ingredients make up less than about 50% of the final personal care product. More typically, the differentiation ingredients will constitute less than about 40%, about 30%, about 25%, about 20%, about 10%, about 5% about 3%, about 2%, about 1% or about 0.5% of the weight of the final personal care product.

Examples of colorants include Red No. 4, Red No. 40 and the FD&C colorants Red No. 3, Red No. 6, Red No. 28, Red No. 33, Blue No. 1, Green No. 5, Yellow No. 5. Oil soluble dyes may also be utilized such as Green No. 6 and D&C Violet No. 2. The levels of these colorants will typically range from about 0.0001% to about 1%, or from about 0.001% to about 0.1% by weight of the total personal care product, although other amounts are contemplated.

Exemplary fragrance ingredients may include one or more of: 2-Methoxy naphthalene; Allyl cyclohexane propionate; alpha-citronellal; alpha-Ionone; alpha-Santalol; alpha-Terpineol; Ambrettolide; Amyl benzoate; Amyl cinnamate; Amyl cinnamic aldehyde; Aurantiol; Benzaldehyde; Benzophenone; Benzyl acetate; Benzyl saticylate; Beta-caryophyllene; beta-Methyl naphthyl ketone; Cadinene; Cavacrol; Cedrol; Cedryl acetate; Cedryl formate; Cinnamyl cinnamate; cis-Jasmone; Coumarin; Cyclamen aldehyde; Cyclohexyl salicylate; d-Limonene; delta-Nonalactone; delta-Undecalactone; Dihydro isojasmonate; Dihydro mycenol; Dimethyl acetal; Diphenyl methane; Diphenyl oxide; Dodecalactone; Ethyl methyl phenyl glycidate; Ethyl undecylenate; Ethylene brassylate; Eugenol; Exaltolide; Galaxolide; gamma-n-methyl ionone; gamma-Undecalactone; Geraniol; Geranyl acetate; Geranyl anthranilate; Geranyl phenyl acetate; Hexadecanolide; Hexenyl salicylate; Hexyl cinnamic aldehyde; Hexyl salicylate; Hydroxycitronellal; Indole; Iso E super; Iso-Amyl salicylate; Iso-Bornyl acetate; Iso-Butyl quinoline; Iso-Eugenol; Laevo-Carvone; Lilial (p-t-bucinal); Linalool; Linalyl acetate; Linalyl benzoate; Methyl cinnamate; Methyl dihydrojasmonate; Methyl-N-methyl anthranilate; Musk indanone; Musk ketone; Musk tibetine; Myristicin; Nerol; Oxahexadecanolide-10; Oxahexadecanolide-11; para-Cymene; para-tert-Butyl cyclohexyl acetate; Patchouli alcohol; Phantolide; Phenyl ethyl alcohol; Phenyl ethyl benzoate; Phenyl heptanol; Phenylhexanol; Phenylethylphenylacetate; Thibetolide; Vanillin; Vertenex; Vetiveryl acetate; Yara-yara; and Ylangene.

Other fragrance ingredients are cyclic and acyclic terpenes and terpenoids, such as, for example, alpha and beta pinene, myrcene, geranyl alcohol and acetate, camphene, dl-limonene, alpha and beta phellandrene, tricyclene, terpinolene, allocimmane, geraniol, nerol, linanool, dihydrolinanool, citral, ionone, methyl ionone, citronellol, citronellal, alpha terpineol, beta terpineol, alpha fenchol, borneol, isoborneol, camphor, terpinen-1-ol, terpin-4-ol, dihydroterpineol, methyl chavicol, anethole, 1,4 and 1,8 cineole, geranyl nitrile, isobornyl acetate, linalyl acetate, caryophyllene, alpha cedrene, guaiol, patchouli alcohol, alpha and beta santalol and mixtures thereof.

Suitable solvents, diluents or carriers for fragrance ingredients, include, for example: ethanol, isopropanol, diethylene glycol monoethyl ether, dipropyl glycol and triethyl citrate.

The fragrance ingredients will generally range from about 0.00001% to about 2%, from about 0.0001% to about 1%, from about 0.01% to about 0.5%, or from about 0.05% to about 0.25% by weight of the personal care product, although other amounts are contemplated.

Vitamins and plant extracts are illustrative of other ingredients that can be added to personal care products. Examples of vitamins include, but are not limited to: Vitamin A (retinol), Vitamin A derivatives (retinyl patmitate, retinyl linoleate, retinyl acetate and retinoic acid), Vitamin C, Vitamin C derivatives (such as ascorbyl tetraisopalmitate and magnesium ascorbyl phosphate), Vitamin E (such as tocopherol acetate), biotin, niacin and DL-panthenol and combinations thereof.

Examples of plants from which extracts and other derivatives can be obtained for use in the present invention include the following: Wormwood (*Artemisia Absinthium*); Acacia (*Robinia pseudoacacia*); Agrimony (*Agrimonia Eupatoria*); Amryllis (Amaryllis); Colombine (*Aquilegia vulgaris*); *Anemone* (*Anemone* spp); Mugwort (*Artemisia vulgaris*); *Arnica* (*Arnica montana*); Sweet Woodruff (*Asperula odorata*); Hawthorn (Crotaegus *oxyacantha*); Azalea (*Azalea* spp); Balsamine (*Impatiens* spp); *Begonia* (*Begonia* spp); *Bougainvillea* (*Bougainvillea* spp); Waterelder (*Viburnum opulus*); Cornflower (*Centaurea Cyanus*); Mullein (*Verbascum* spp); Common heather (*Calluna vulgaris*); Barbary fig (*Opuntia vulgaris*); Camellia (*Camellia japonica*); Chamomile (*Anthemis nobilis*); Campanuta (*Campanula* spp); Large Indian Cress (Tropeolum *majus*); Safflower (*Carthamus tinctorius*) (*Catalpa* bignomioides); Star thistle (*Centaurea calcitrapa*); Rough Cherry (*Prunus cerasus*); Honeysuckle (*Lonicera* spp); Daisy (*Chrysanthemum* Leucoanthemum); Travelle's Joy (*Clematis vitalba*); Quince (*Cydonia* vulgaris); Red poppy (*Papaver Rhoeas*); Cotchicum or Meadow Saffron (Cotchicum automnale saffron); Cornel tree (or dogwood) (*Cornus* spp); *Crocus* (*Crocus* spp); *Cyclamen* (*Cyclamen* spp); *Dahlia* (*Dahlia variabilis*); Field larkspur (*Delphinium consolida*); Dulcamara (Sotanum *Dulcamara*) (*Leontopodium Alpinum*); Dog rose (*Rosa canina*); Fumitory (*Fumaria officinalis*); Broom (*Cytisus scoparius*); Gentian (*Gentiana* spp); *Geranium* (*Geranium* spp); Wallflower (Cheirantus *cheiri*); Sword-lily (Gladialus spp); Marsh Mallow (Althaea *officinalis*) (*Gypsophila* spp); Roselle (Hibiscus spp); *Hydrangea* (*Hydrangea* spp); Hops (*Humulus lupulus*); Live ever (Helicrysum *arenarium*); Garden balsam (*Impatiens* spp); Orrice (*Iris* spp); Hyacinthe (Hyacynthus spp); Jasmine (*Jasminum* spp); Jonquil (*Narcissus jonquilla*); *Oleander* (*Nerium oleander*); Lavender (Lavandule *officinalis*) (*Lavatera* spp); Lilac (*Syringa vulgaris*); White lily (*Lilium candidum*); Bindweed (Conedvalus spp); Lupin (*Lupinus albus*); *Magnolia* (*Magnolia* spp); Daisy (*Chrysanthemum leucanthemum*); Horsechestnut (*Aesculus Hippocastanum*); Wild chamomile (*Matricaria chamomilla*); Mallow (*Malva* spp); Melilot (*Melilotus officinalis*); Mint (*Mentha* spp); St John's Wort (*Hypericum perforatum*); *Mimosa* (*Mimosa* spp); Lion's mouth (*Antirrhinum majus*); Mugget (*Convallaria maialis*); *Myosotis* (*Myosotis* spp); Daffodil (*Narcissus* spp); White water Lily (*Nymphaea alba*); Gilower (*Dianthus caryophyllus*); Marigold (*Tagetes* spp); Sweet orange Tree (*Citrus Aurantium*); Orchid; Daisy (*Bellis perennis*); Passion flower (*Passiflora* spp); Peach-tree (*Prunus persica*); *Pelargonium* (*Pelargonium* spp); Pansy (*Viola* spp); Snowdrop (*Galanthus nivalis*); Periwinkle (*Vinca* spp); *Petunia* (*Petunia* spp); *Phlox* (*Phlox* spp); Field larkspur (*Delphinium consolida*); Garden peony (*Paeonia officinalis*); Sweat pea (*Lathyrus* odorantes) (*Polygonum* spp); Apple tree (*Pirus malus*); Primrose (*Primula* spp); Silver weed (Potentille *Anserina*); Plum-tree (*Prunus domestica*); Pyrethum (*Chrysanthemum* cineriaefolium); Meadow Sweet (*Spiraea Ulmaria*); Buttercup (Ranuncukus spp); *Rhododendron* (*Rhododendron ferrugineum*); Rose mary (*Rosmarinus officinalis*); French Rose (Rose gattica); Saffron (*Crocus sativus*); Grass potty (*Lythrum* saticaria); Bloodroot (*Sanguinaria canadiensis*); Soapwort (*Saponaria* officinatis); Sage (*Salvia officinalis*); Willow (*Salix alba*); Devil's bit scabiou (*Scabiosa Succisa*); *Syringa* (*Philadelphus coronarius*); Serpollet (*Thymus* serpylum) (*Sophora japonica*); Corme (*Sorbus domestica*); Marigold (Catandula officinatis); *Spiraea* (*Spiraea* spp); Elder (*Sambucus nigra*); Tamarisk (Tamaris *gallica*); Tansy (Tanatecum vutgare); Garden thyme (*Thymus vulgaris*); Lime (*Tilia* spp); Clover (Trifotium spp); Tulip (Tutipa spp); Coltsfoot (Tussitago larfara); Speedwell (*Veronica officinalis*); Common vervain (*Verbena* officinatis); Violet (*Viola* spp); and *Yucca* (Yuccas spp).

The amount of vitamin and/or plant extract ingredients may vary depending on the desired end product, but typically will range from about 0.00001% to about 2%, from about 0.0001% to about 1%, or from about 0.001 to about 0.5% by weight of the total personal care product.

A unique aspect of the present invention is that the viscosity of the base composition is measured and, if needed, adjusted to a predetermined range before the base composition is mixed with the one or more differentiation ingredients. The predetermined viscosity range is calculated based on the estimated or measured effects of the differentiation ingredients on the base composition. Thus, once the differentiation ingredients are added to the base composition, the resulting composition will have a final viscosity that is within the desired final composition viscosity range and no additional trimming is required. This is very different from current practices where viscosity modifications are made after all of the ingredients of the final formula are combined and generally just prior to the filling machine. When the final product viscosity is managed this way, however, the speed of the overall process can be negatively impacted because of the time it takes time to trim the final product before it can be sent to the filling station. Often this leads to downtime for the fillers and packing machines, which adds to the cost of the product.

In order to best achieve the benefits of the present invention for the examples described in the EXAMPLES section, below, the viscosity of the base composition will generally range from about 10 cps to about 8,500 cps. More particularly, the base viscosity may range from about 100 cps to about 8,000 cps, about 100 cps to about 2,400 cps, or from about 1,000 cps to about 7,500 cps. Viscosities of the resultant personal care product normally range between about 1,000 and about 40,000 cps, between about 2,000 cps and about 35,000 cps, between about 2,500 cps and about 30,000 cps, between about 2,500 cps and about 20,000 cps, or between about 8,000 cps and about 25,000 cps. All viscosity measurements set forth in the examples are measured with a Brookfield RS Viscometer, Cone C75 a shear rate of 2/s for 3 minutes at 26° C.

Of course, these preferred viscosity values could be different for different personal care products, but the general process is the same: 1) formulate a base composition; 2) measure a first viscosity after the base composition is formed; 3) compare the first viscosity with a predetermined desired base viscosity; 4) if the first viscosity is not within the range of the predetermined desired base viscosity range, adjust the viscosity of the base to a second viscosity that is within the predetermined viscosity range (this can happen in a single step or multiple steps so long as the end result is that the second viscosity is within the predetermined desired base viscosity range); and 5) add one or more product differentiation ingredients. The result is a final product having a viscosity within the desired end product range without the need for additional trimming. This allows for a more efficient system and reduces the need to slow down the process to allow for trimming the final product and/or downtime for the filling and packing machines. Of course, it is contemplated that some fine trimming might be desired or required after the ingredients are all combined, but that is generally not preferred and typically, the second viscosity would be adjusted to eliminate the need for any fine tuning of future batches and/or runs.

The present method may also be used to more efficiently control the pH of a composition. Similar to the process described for viscosity, the pH of the base can be measured and, if needed, adjusted to a second pH before any product differentiation ingredients are added to the base composition. The second pH can be calculated to be in a range so that once the product differentiation ingredients are added, the final pH is within a desired final composition pH range. As such, it is possible that no additional pH modification will be necessary after the differentiation ingredients are combined with the base composition. However, if the final pH is not within the desired final composition pH range, the combined composition can be further trimmed to move the pH into the desired final pH range quickly and without the addition of significant amounts of pH modifiers. As with viscosity, performing this method can speed up the overall process, reduce costs and/or reduce equipment downtime.

FIG. 1 is a schematic diagram of the equipment and process that may be used to achieve the benefits of the present invention. Specifically, FIG. 1 shows an example of a batch process for formulating a personal care product. As shown, a first mixing vessel 5, such as first mixing tank 10 is provided. The ingredients of the base composition are measured into the first mixing tank 10 and mixed to the desired homogeneity. First mixing tank 10 may include an agitation mechanism 15 such as one or more a paddle stirrers, sonic agitators, pumping systems, baffles or combinations thereof. The first mixing tank 10 may also include a heating or cooling mechanism. A more detailed description of an exemplary mixing tank 10 suitable for use in the disclosed process is further described below and shown in FIG. 3.

Once the base composition is mixed to the desired extent, its viscosity is measured and compared to a predetermined viscosity range based on the desired final product viscosity and the affect that the differentiation ingredients will have on the viscosity of the base composition. If needed, the viscosity of the base is modified to a second viscosity that falls with the predetermined viscosity range. It is then moved to a storage vessel 30, such as storage tank 35. A pump 20 may be used to move the base composition from the first mixing tank 10 to the storage tank 35, through a pipe 25. Alternatively, the base composition may be poured directly from the first mixing tank 10 into the storage tank 35 or moved thereto by means other than a pump, including, but not limited to gravity, by means of another tank and/or by any other method of moving the base composition to the storage tank 35. The storage tank 35 is configured to store the base composition until the manufacturer is ready to perform additional processing steps on the base formulation, such as mixing in differentiation ingredients to produce the final personal care product. The storage tank 35 may be a single tank or multiple tanks or other vessels that are connected to each other or separate.

As with the first mixing tank 10, the storage tank 35 may be operatively associated with a pump 20 that can move the base composition from the storage tank 35 to equipment used to further process the base composition having the modified viscosity. For example, the base composition having the modified viscosity may be moved to a second mixing vessel 50 such as a second mixing tank 55 that includes a mixing mechanism such one or more paddle stirrers, sonic agitators, pumping systems, baffles or combinations thereof. The second mixing tank 55 may also include a heating or cooling mechanism.

While residing in the second mixing tank 55, one or more differentiation ingredients are added to the base composition having the modified viscosity. The differentiation ingredients may be obtained from one or more tanks, such as differentiation ingredient storage tanks 60 and 70 or from other storage and/or transportation vessels. The base composition with the modified viscosity and one or more differentiation ingredients are mixed together in the second mixing vessel 50. The viscosity of resulting mixture should fall within the desired final product viscosity range. As such, the final personal care product can be moved immediately to another storage vessel, such as final product storage tank, or directly to filling and packing machine, such as filler 110. In either case, one or more additional pumps 20 or other transport mechanisms can be used to help move the final personal care composition to the filler or other processing equipment.

It is contemplated that the step of adding one or more differentiation ingredients can take place as the base composition with the modified viscosity is directed into individual packages or after it is fully within a package. In such embodiments, the packages may be subjected to vibration, shaking, or other movement to ensure proper mixing of the ingredients. This type of process is especially useful for personalized or customized products where the batch size is very small (e.g. 1-100), but can also be used for larger batch sizes where it is advantageous to add the differentiation ingredients only after the base with the modified viscosity is measured into individual packages.

Figure 2:
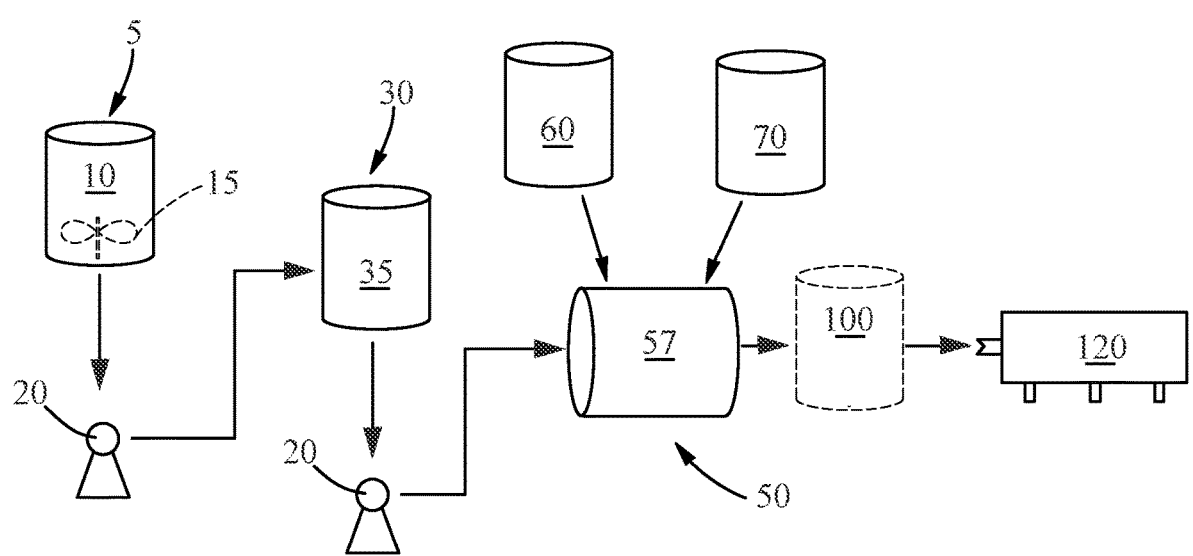
FIG. 2 is a schematic flow diagram of a second example of the new process.

FIG. 2 shows an alternative process in accordance with the present invention. The key difference is that the process shown in FIG. 2 is a semi-continuous process as opposed to the batch process shown in FIG. 1. A fully continuous process is also contemplated where the base composition is continuously formulated prior to it being mixed with the differentiation ingredients.

As shown, similar to the batch process shown in FIG. 1, the process shown in FIG. 2 includes a first mixing vessel 5, such as first mixing tank 10. The ingredients of the base composition are measured into the first mixing tank 10 and mixed to the desired homogeneity. As with respect to the batch process, the first mixing tank 10 of the continuous or semi-continuous process may include an agitation mechanism 15 such as a paddle stirrer, sonic agitator, pumping system, baffles or combinations thereof. The first mixing tank may also include a heating or cooling mechanism.

Again, similar to the process shown in FIG. 1, once the base composition is mixed to the desired extent, its viscosity is measured and compared to a predetermined viscosity range based on the desired final product viscosity and the affect that the differentiation ingredients will have on the viscosity of the base composition. If needed, the viscosity if the base is modified to a second viscosity that falls with the predetermined viscosity range. It is moved to a storage vessel 30, such as storage tank 35. A pump 20 may be used to move the base composition from the first mixing tank 10 to the storage tank 35, through a pipe 25. Alternatively, the base composition may be poured directly from the first mixing tank 10 into the storage tank 35 or moved thereto by means other than a pump, including, but not limited to gravity, by means of another tank and/or by any other method of moving the base composition to the storage tank 35. The storage tank 35 is configured to store the base composition until the manufacturer is ready to perform additional processing steps on the base formulation, such as mixing in differentiation ingredients to produce the final personal care product. The storage tank 35 may be a single tank or multiple tanks or other vessels that are connected to each other or separate.

The storage tank 35 may be operatively associated with a pump 20 that can move the base composition from the storage tank 35 to equipment used to further process the base composition. For example, in this semi-continuous process, the base composition may be moved to a second mixing vessel 50 such as a continuous blender 57. Alternative second mixing vessels 50 for semi-continuous processes include static mixers, orifice mixers, blending tubes or homogenizers (e.g. Sonolator®). While residing in the second mixing vessel 50, one or more differentiation ingredients are added to the base composition. The differentiation ingredients may be obtained from one or more tanks, such as differentiation ingredient storage tanks 60 and 70 or from other storage and/or transportation vessels. The base composition and one or more differentiation ingredients are mixed together in the second mixing vessel 50. The viscosity of resulting mixture should fall within the desired final product viscosity range. As such, the final personal care composition may be moved immediately to another storage vessel, such as final product storage tank 100, or directly to filling and packing machine, such as filler 120. In either case, one or more additional pumps 20 or other transport mechanisms can be used to help move the final personal care composition to the filler or other processing equipment.

As with the process shown in FIG. 1, the process shown in FIG. 2 may also be performed in such a way that the step of adding one or more differentiation ingredients takes place as the base composition with the modified viscosity is directed into individual packages or after it is fully within a package.

Figure 3:
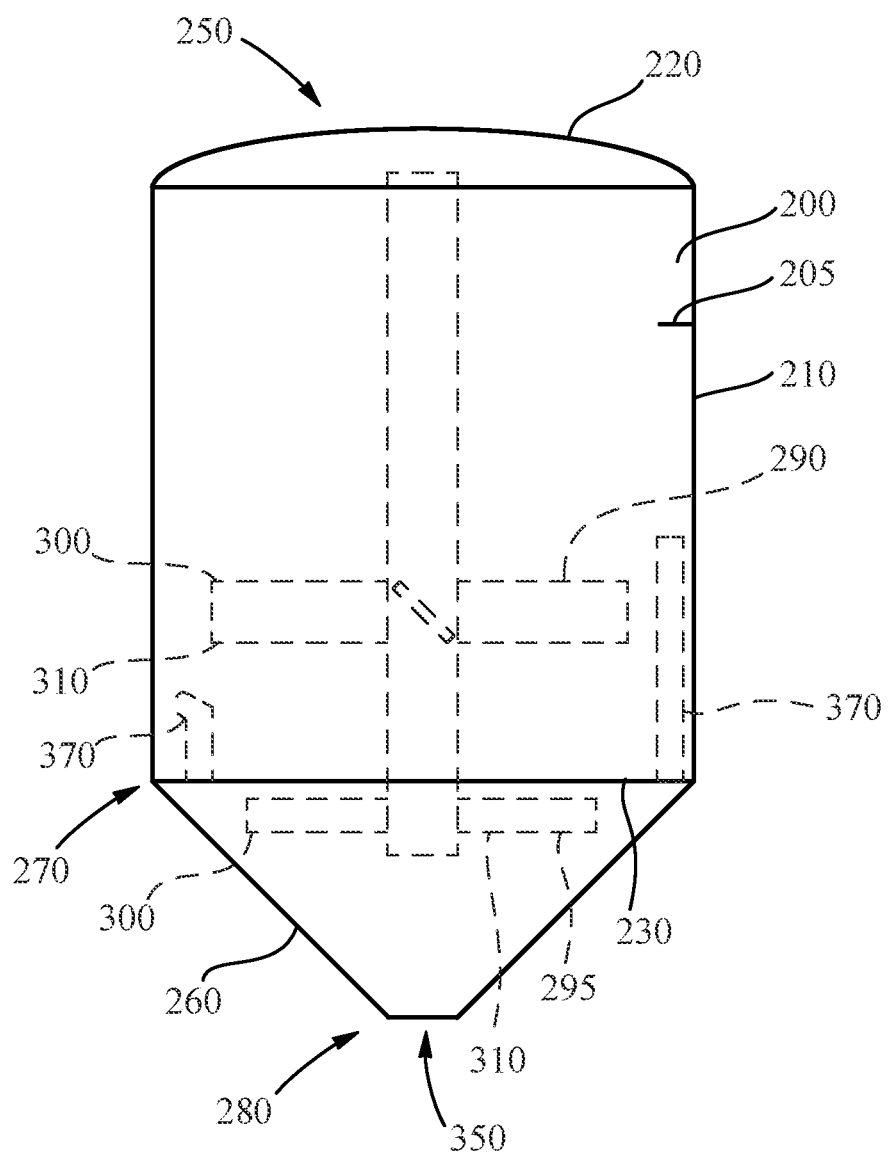
FIG. 3 is a cross-section of an example of a mixing tank that can be used with the new process described herein.

FIG. 3 shows just one example of a suitable mixing tank that may be used with the disclosed process. The figure and description are not intended to be limiting as other mixing tanks and/or mixing vessels can be used, as desired. The mixing tank 200 shown includes a continuous generally vertical wall 210 made from one or more portions, the continuous vertical wall 210 extending from a wall top 220 to a wall bottom 230 and surrounding a reservoir 250, the reservoir 250 having a working volume defined by a predetermined liquid fill level for a full batch. The tank 200 has a generally conical base 260 having a large diameter end 270 and a small diameter end 280, the large diameter end 280 of the conical base 260 being integral with or joined to the wall bottom 230 and extending downward from the wall bottom 230 with the smaller diameter end 280 of the conical base 260 farthest from the wall bottom 230, wherein the reservoir 250 extends into the conical base 260.

The tank 200 may include one or more agitation mechanisms for mixing the ingredients that are directed into the tank, such as, for example, impellers. As shown, the tank 200 includes a first impeller 290 and a second impeller 295, disposed within the reservoir 250. Each impeller has an upper side 300 and a lower side 310, the upper side disposed closer to the wall top 220 than the lower side 310. The lower side 310 of the second impeller 295 is disposed between the small diameter end 280 and the large diameter end 270 of the conical base 260. The first impeller 290, on the other hand, is disposed at least partially within in the reservoir 250 outside of the conical base 260. It may be desired that the first impeller 290 is disposed within the reservoir 250 such that it is partially or completely below the fill level 205 for the tank 200. For example, it may be desirable that none of the impellers are disposed above 90%, 80%, 70%, 60%, 50% or 40% of the fill level 250. This can help ensure that unwanted air is not mixed into the composition being mixed if less than a full batch is being produced. For example, the tank 200 can be used to produce batch sizes that are from about 25%, 30%, 40%, 50%, 60%, 70%, 80% 90% or 100% of a full batch size without causing unacceptable amounts of aeration in the mixture. The impellers 290, 295 may be any desired shape or size, and for example, may be helical or non-helical. If non-helical, the impellers may be pitched blade, turbine-type impellers having any desired pitch. The impellers 290, 295 may be have the same shape and dimensions (e.g. diameter, height, thickness, pitch) or may be different in one or more characteristics.

The tank 200 may also include one or more baffles 370. The baffles 370 may be fixed and if more than one is used, they may be of the same or different shapes and/or lengths. For example, it may be desired that the baffles 370 extend from close to the wall bottom 230 to close to the wall top 220. Alternatively, it may be desirable that one or more of the baffles 370 not extend beyond a certain height from the wall bottom 230. For example, it may be desirable that at least one or none of the baffles 370 extend beyond 90%, 80%, 70%, 60%, 50% or 40% of the distance between the wall bottom 230 and the fill level 205.

The mixing tank 200 may include one or more orifices for filling or draining the tank 200. For example, the tank 200 may include an exit orifice 350 disposed at the small diameter end 280 of the conical base 260. The mixing tank 200 may have any desired working volume. For commercial applications, the tank 200 will typically have a volume of at least 100 kg. The tank 200 can be stationary or moveable and may be made out of any suitable material based on the desired use.

EXAMPLES

The following examples will more fully illustrate the embodiments of this invention. All parts, percentages and proportions referred to herein and in the appended claims are by weight unless otherwise illustrated.

Example 1

This example describes the process that can be used to create a shampoo wherein the desired final shampoo viscosity is between about 15,000 cps and about 19,000 cps. The predetermined desired base viscosity for this formula is about 4,500 cps to 6,500 cps. The ingredients used in the shampoo of this example and their weight percentages are listed in Table 1.

First, an Ethylene Glycol Distearate crystalline premix is made. To make the premix, about 20% to about 35% of the total amount of Sodium Lauryl Sulfate that is in the final shampoo formula is added to water (a portion of the total water shown in Table 1) for processability and the mixture is heated to a temperature of about 60 C to 80 C. The ingredients are mixed with slow agitation to form a surfactant solution. The salts and pH modifiers (i.e. Sodium Benzoate, Tetrasodium EDTA, Citric Acid) are added to the solution at the percentages shown in Table 1, below. They are allowed to dissolve until the pH of the mixture is approximately 4.5 to 7. Ethylene Glycol Distearate is added at the level as shown in Table 1 and allowed to melt. The mixture is cooled to a temperature of between about 25 C and about 40 C forming the Ethylene Glycol Distearate crystalline premix.

A shampoo base is made in a first making vessel by adding the Guar Hydroxypropyltrimmonium Chloride to water (the remaining amount of water in Table 1 that was not used in the Ethylene Glycol Distearate premix) and mixing it into a slurry. Then, the Sodium Laureth-3 Sulfate, the remaining amount of Sodium Lauryl Sulfate, the Piroctone Olamine and all other ingredients, including the Ethylene Glycol Distearate premix material described above, are added to the slurry. The pH is adjusted to approximately 5 to 7 with citric acid, forming the shampoo base.

TABLE 1

| Ingredient | Weight Percent |
| --- | --- |
| Water | 29.78 |
| Sodium Laureth-3 Sulfate, 29% active | 30 |
| Sodium Lauryl Sulfate, 29% active | 26 |
| Cocamidopropyl Betaine, 30% active | 7 |
| Guar Hydroxpropyltrimmonium Chloride | 0.28 |
| Sodium Benzoate | 0.3 |
| Tetrasodium EDTA | 0.18 |
| Citric Acid | 0.5 |
| Methylchloroisothiazolinone | 0.035 |
| Piroctone Olamine | 0.625 |
| Ethylene Glycol Distearate | 1.6 |
| Dimethiconol and Dimethicone and TEA-Dodecylbenzenesulfonate* | 3.5 |
| Sodium Chloride | 0.2 |

*Available from Wacker Chemical as Belsil DM5500.

Once the base is formed, a first viscosity is taken. The first viscosity is compared to the predetermined desired base viscosity range of about 4,500 cps to 6,500 cps. If the first base viscosity is not within the predetermined desired base viscosity range, sodium chloride (viscosity modifier) is added to increase viscosity or sodium xylene sulfonate (viscosity modifier) is added to decrease the base viscosity to be within the predetermined desired range for the base viscosity. In this example, for illustration purposes, we will consider the measured first viscosity of the base to be 4,639 cps. Since the first viscosity is within the predetermined desired base viscosity, no adjustments are needed or made. The shampoo base having its measured viscosity within the predetermined desired base viscosity range is moved to a second vessel, which can be immediately before a filler or elsewhere in the process, if desired. In the second vessel, the following ingredients listen in Table 2, below are added to the base as late product differentiating ingredients.

TABLE 2

| Ingredient | Weight Percent |
| --- | --- |
| Shampoo Base | 95.92 |
| Perfume | 0.88 |
| Sodium Chloride | 0.2 |
| Water | 3.0 |

The final shampoo viscosity is measured for the purposed of this example. In this example, for illustration purposes, we will consider the final measured shampoo viscosity to be 15,785 cps. The final shampoo viscosity is within the desired range.

Example 2

The same formula and making procedure as in Example 1 is used, but the final shampoo desired viscosity for a different consumer target is 9,500 cps to 12,500 cps. The predetermined desired base viscosity for this formula is about 2,000 cps to about 3,500 cps.

As in example 1, a shampoo base is made and tested for a first viscosity. In this example, for illustration purposes, we will consider the measured first viscosity to be 4,639 cps. Because the viscosity is not within the predetermined desired base viscosity range (2,000 cps to 3,500 cps), the base is modified by the addition of 0.5% sodium xylene sulfonate. The ingredients are mixed and a second viscosity measurement is taken and compared to the predetermined desired base viscosity. For the purposes of this example, for illustration purposes, we will consider the measured second viscosity to be 3,421 cps. Since this is within the predetermined desired base viscosity of 2,000 cps to 3,500 cps, no additional viscosity modifiers are added. However, if the second viscosity is still not within the predetermined desired base viscosity range, additional viscosity modifiers can be added to further adjust the viscosity of the base to be within the predetermined desired base viscosity range. This can be done as many times is as needed to get the second viscosity of the base into the predetermined desired base viscosity range.

The base with the desired second viscosity is finished into shampoo by adding one or more late differentiating ingredients. For the purposed of this example, for illustration purposes, we will consider the measured final shampoo viscosity to be 12,132 cps. The final shampoo viscosity is within the final shampoo desired viscosity range of 9,500 cps to 12,500 cps due to pre-determination of the desired base shampoo viscosity and adjusting the viscosity of the base, as needed, to be within the desired base shampoo viscosity prior to adding the late differentiating ingredients.

Example 3

This example describes the process that can be used to create a shampoo wherein the desired final shampoo viscosity is between about 10,000 cps and 14,000 cps. The predetermined base viscosity for this formula is about 5,000 cps to 7,500 cps. The ingredients used in the shampoo and their weight percentages are listed in Tables 3 and 4.

First, a premix of Trihydroxystearin is made by adding a suitable amount of Sodium Laureth-1 Sulfate to emulsify the Trihydroxystearin to a vessel. Trihydroxystearin is added and the vessel is heated to a point where the Trihydroxystearin is incorporated with the Sodium Laureth-1 Sulfate. The premix is then cooled to ambient temperature.

Next, a premix of Fatty Alcohol is made by heating sufficient Sodium Laureth-1 Sulfate and water are heated above the melting point of Cetyl Alcohol and Stearly Alcohol. Cetyl Alcohol and Stearyl Alcohol are added and mixed. The vessel is cooled with agitation to ambient temperature.

A shampoo base is made in a first making vessel by adding the remaining amount of Sodium Laureth-1 Sulfate and Tetrasodium EDTA and mixed. The Guar Hydroxypropyltrimonium Choride and the remaining amount of water are slurried together and then added to the vessel. The Citric Acid, Sodium Benzoate, and Salicylate are added to the vessel. Cocamidopropyl Betaine, the premix of Trihydroxystearin and the premix of Fatty Alcohol are added. Then, Polyquaternium-6, water, and Sodium Chloride are added to the vessel.

TABLE 3

| Ingredient | Weight Percent |
| --- | --- |
| Sodium Laureth-1 Suflate | 60.0 |
| Tetrasodium EDTA | 0.1 |
| Guar Hydroxypropyltrimonium * | 0.21 |
| Water | 29.01 |
| Citric Acid | 0.62 |
| Sodium Benzoate | 0.55 |
| Sodium Salicylate | 0.32 |
| Trihydroxystearin | 0.12 |
| Cetyl Alcohol | 0.86 |
| Stearyl Alcohol | 1.53 |
| Cocamidopropyl Betaine | 5.9 |
| Polyquaternium-6 ** | 0.66 |
| Sodium Chloride | 0.12 |

* Available as N-Hance 3196 from Ashland Chemical
** Available as Mirapol 100S from Solvay Once the base is formed, a first viscosity is taken. The first viscosity is compared to the predetermined desired base viscosity range of about 5,000 cps to 7,500 cps. If the first base viscosity is not within the predetermined desired base viscosity range, sodium chloride (viscosity modifier) is added to increase viscosity or sodium xylene sulfonate (viscosity modifier) is added to decrease the base viscosity to be within the predetermined desired range for the base viscosity. In this example, for illustration purposes, we will consider the measured first viscosity of the base is 7,240 cps. Since the first viscosity is within the predetermined desired base viscosity range, no adjustments are needed or made. The shampoo base having its measured viscosity within the predetermined desired base viscosity range is moved to a second vessel, which can be immediately before a filler or elsewhere in the process, if desired. In the second vessel, the following ingredients listed in Table 4, below, are added to the base as late product differentiating ingredients.

TABLE 4

| Ingredient | Weight Percent |
| --- | --- |
| Shampoo Base | 96.00 |
| Perfume | 0.70 |
| Water | 3.30 |

The final shampoo viscosity is measured. In this example, for illustration purposes, we will consider the measured final shampoo viscosity to be 13,173 cps. The final shampoo viscosity is within the desired viscosity range of 10,000 cps to 14,000 cps.

Example 4

This example describes the process that can be used to create a sulfate free shampoo wherein the desired final shampoo viscosity is between about 2,500 cps and 6,500 cps. The predetermined base viscosity for this formula is about 1,400 cps to 6,500 cps. The ingredients used in the shampoo and their weight percentages are listed in Table 5 and 6.

A sulfate free shampoo base is made in a first making vessel by adding a suitable amount of water. The vessel is heated to above the melting point of Sodium Cocoyl Isethionate. Sodium Cocoyl Isethionate is added and mixed until melted. Sodium Benzoate, Tetrasodium EDTA, Sodium Salicylate, Lauramidopropyl Betaine, Sodium Lauroyl Sarcosinate, Trisodium Citrate Dihydrate and a slurry of the remaining water and Polyquaternium-10 are added and the vessel. The vessel is cooled to ambient temperature. The pH is adjusted to approximately 5.5 to 6.0 with citric acid.

TABLE 5

| Ingredient | Weight Percent |
| --- | --- |
| Water | 47.80 |
| Sodium Cocoyl Isethionate | 6.67 |
| Lauramidopropyl Betaine ** | 31.00 |
| Sodium Lauroyl Sarcosinate | 9.25 |
| Tetrasodium EDTA | 0.18 |
| Citric Acid | 0.71 |
| Sodium Benzoate | 0.83 |
| Sodium Salicylate | 0.5 |
| Trisodium Citrate Dihydrate | 2.78 |
| Polyquaternium-10 * | 0.28 |

* Available as JR-30M from Union Carbide Amerchol
** Available as Mackam DAB ULS from Solvay Once the base is formed, a first viscosity is taken. The first viscosity is compared to the predetermined desired base viscosity range of about 1,400 cps to 6,500 cps. If the first base viscosity is not within the predetermined desired base viscosity range, citric acid (pH and viscosity modifier) is added to increase viscosity and decrease the pH to be within the predetermined desired range for the base viscosity and pH. Care should be taken to not add an excess of Citric Acid resulting in either the pH or viscosity to be out of the desired range. In this example, for illustration purposes, the measured first viscosity of the base is 6,430 and pH to be 5.55. Since the first viscosity and pH are within the predetermined desired base viscosity range, no adjustments are needed or made. The shampoo base having its measured viscosity within the predetermined desired base viscosity range is moved to a second vessel, which can be immediately before a filler or elsewhere in the process, if desired. In the second vessel, the following ingredients listed in Table 6, below, are added to the base as late product differentiating ingredients.

TABLE 6

| Ingredient | Weight Percent |
| --- | --- |
| Sulfate Free Shampoo Base | 90.00 |
| Perfume | 1.10 |
| Water | 8.90 |

The final shampoo viscosity is measured for the purpose of this example. In this example, for illustration purposes, we will consider the measured final shampoo viscosity to be 6,130 cps. The final shampoo viscosity is within the desired viscosity range of 2,500 cps and 6,500 cps.

Example 5

In this example, the same formula and method of manufacture are used as in Example 4. The difference is the base pH was adjusted to 5.72 with 0.60% Citric Acid rather than 0.71% Citric Acid in example 4. As a result of the lower Citric Acid level, the base pH is higher at 5.72 rather than 5.55 as in Example 4. The first viscosity is compared to the predetermined desired base viscosity range of about 1,400 cps to 6,500 cps. In this example, for illustration purposes, we will consider the measured first viscosity of the base to be 3,900 cps. Since the first viscosity and pH are within the predetermined desired base viscosity range, no adjustments are needed or made. The shampoo base having its measured viscosity within the predetermined desired base viscosity range is moved to a second vessel, which can be immediately before a filler or elsewhere in the process, if desired. In the second vessel, the following ingredients listed in Table 7, below, are added to the base as late product differentiating ingredients.

TABLE 7

| Ingredient | Weight Percent |
| --- | --- |
| Sulfate Free Shampoo Base | 90.00 |
| Citric Acid | 0.11 |
| Perfume | 1.10 |
| Water | 8.79 |

The final shampoo viscosity is measured for the purpose of this example. In this example, for illustration purposes, we will consider the measured final shampoo viscosity to be 6,130 cps, the same as in Example 4. The final shampoo viscosity is within the desired viscosity range of 2,500 cps and 6,500 cps. The final shampoo pH is measured as 5.55, the same as in Example 4. Table 8, below, shows a comparison between example 4 and example 5.

TABLE 8

| | Example 4 | Example 5 |
| --- | --- | --- |
| Base Citric Acid (wt %) | 0.71 | 0.60 |
| Base pH | 5.50 | 5.72 |
| Base Viscosity (cps) | 6430 | 3900 |
| Second Vessel Citric Acid added (wt %) | 0.00 | 0.11 |
| Total Citric Acid Added (wt %) | 0.71 | 0.71 |
| Final Shampoo pH | 5.55 | 5.55 |
| Final Shampoo Viscosity (cps) | 6130 | 6130 |

Different base pH and Citric Acid level are used in Example 5 vs. example 4. Adding the adjustable material Citric Acid to the second vessel, as in Example 5, is done to enable a wider range of formula options using the same base. For example, if some formulas require different amounts of an adjustable like Citric Acid to achieve the desired pH and viscosity limits this can more efficiently be managed by adding an adjustable to the second vessel.

Making many formulas from the same base is desired since the higher the number of final formulas that can be made from a common base the fewer the number of bases needed to support a range of formulas. Fewer bases can be more efficient as fewer storage vessels, washout or transitions between bases are needed. Adding Citric Acid or another modifier enables a wider range of formulas to be made from the same base since some materials, for example perfumes, impact viscosity differently and some materials, for example botanical blends, impact pH differently. As a result, different amount of an adjustable might be needed to meet pH and viscosity ranges.

While particular embodiments of the present disclosure have been illustrated and described, it would be obvious to those skilled in the art that various other changes and modifications can be made without departing from the spirit and scope of the disclosure. It is therefore intended to cover in the appended claims all such changes and modifications that are within the scope of this disclosure.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A process for manufacture of personal care compositions, including late-stage differentiation of the personal care composition from a base composition, the process comprising:
    a) formulating a batch of the base composition in a first vessel, the batch of the base composition being an aqueous mixture of at least one surfactant and water and having a first viscosity;
    b) measuring the first viscosity of the batch of the base composition;
    c) comparing the first viscosity of the batch of the base composition to a predetermined desired base viscosity range;
    d) if the viscosity of the batch of the base composition is outside the predetermined desired base viscosity range, adjusting the viscosity of the batch of the base composition to a second viscosity that is within the desired base viscosity range by addition of one or more viscosity modifiers;
    e) moving the batch of the base composition with the second viscosity to a second vessel; and
    f) adding one or more differentiation compositions to the base composition creating the personal care composition, wherein the personal care composition has a final viscosity that is different from the second viscosity.

2. The process of claim 1 wherein the final viscosity is within a desired final viscosity range.

3. The process of claim 1 wherein the predetermined desired base viscosity is determined based on the desired final viscosity range.

4. The process of claim 1 wherein the base composition includes a sulfated or a sulfate-free surfactant.

5. The process of claim 1 wherein the base composition includes a sulfate-free surfactant selected from the group comprising: taurates, isethionates, glycinates, glycosides, glutamates, betaines, sulfonates, sulfosuccinates, sulfoacetates, sarcosinates, alaninates, carboxylates, and rhamnolipids.

6. The process of claim 1 wherein the base composition includes a sulfated surfactant and the second viscosity is between about 1,000 cps and about 7,500 cps.

7. The process of claim 6 wherein the final viscosity is between about 8,000 cps and about 25,000 cps.

8. The process of claim 1 wherein the base composition includes a sulfate-free surfactant and the second viscosity is between about 100 cps and about 2,400 cps.

9. The process of claim 8 wherein the final viscosity is between about 2,500 cps and about 20,000 cps.

10. The process of claim 1 wherein the change in viscosity from the second viscosity to the final viscosity is due to the addition of the one or more differentiation compositions.

11. The process of claim 10 wherein no additional viscosity modifiers other than the one or more differentiation compositions are added to personal care composition after the differentiation compositions are added to the base composition.

12. The process of claim 1 wherein step d) includes adding 0.01% to about 5% viscosity modifiers by weight of the base composition.

13. The process of claim 12 wherein the viscosity modifiers are selected from the group consisting of: sodium chloride, potassium chloride, citric acid, sodium citrate, HCl, NaOH, sodium xylene sulfonate, dipropylene glycol, and glycerine.

14. The process of claim 1 wherein the base composition has a first pH and the pH is modified to a second pH before the base composition is moved to the second vessel.

15. The process of claim 14, wherein after the differentiation compositions is added to the base composition, the combined composition has a final pH that is different from the second pH.

16. The process of claim 15 wherein the final pH is within a desired final pH range.

17. The process of claim 1 wherein the base composition is at least 90% of the weight of the total weight of the personal care composition.

18. The process of claim 1 wherein the total of the one or more differentiation compositions is no greater than 10% by weight of the personal care composition.

19. The process of claim 1 wherein the one or more differentiation compositions includes at least one perfume.

20. The process of claim 1 wherein the final viscosity of the personal care composition is at least about 15% greater or less than the second viscosity of the base composition.

* * * * *